United States Patent
Lawlor et al.

(10) Patent No.: US 6,368,866 B1
(45) Date of Patent: Apr. 9, 2002

(54) RAPID SEPARATION ASSAY FOR TOTAL IRON BINDING CAPACITY

(75) Inventors: Joseph F. Lawlor, Arlington; Joseph D. Musto, Dover; Gordon Siek, Somerville, all of MA (US)

(73) Assignee: Reference Diagnostics, Inc., Bedford, MA (US)

( * ) Notice: Subject to any disclaimer, the term of this patent is extended or adjusted under 35 U.S.C. 154(b) by 0 days.

(21) Appl. No.: 09/364,702

(22) Filed: Jul. 30, 1999

Related U.S. Application Data

(60) Provisional application No. 60/095,107, filed on Aug. 3, 1998.

(51) Int. Cl.[7] .............................................. G01N 33/50
(52) U.S. Cl. .......................... 436/74; 436/84; 436/518; 436/524; 436/525; 436/526
(58) Field of Search .................... 436/12, 16, 8, 436/74, 84, 518, 523–526

(56) References Cited

U.S. PATENT DOCUMENTS

| | | | | |
|---|---|---|---|---|
| 3,773,467 A | * | 11/1973 | Yang et al. ................. 250/303 |
| 3,887,332 A | | 6/1975 | Takase et al. ................ 436/12 |
| 3,899,472 A | | 8/1975 | Aya et al. .................... 525/310 |
| 3,925,020 A | | 12/1975 | Ogawa et al. ............... 250/303 |
| 3,981,776 A | | 9/1976 | Saxholm ...................... 422/69 |
| 4,139,604 A | * | 2/1979 | Gutcho et al. .............. 436/541 |
| 4,224,034 A | | 9/1980 | Denney et al. .............. 436/84 |
| 4,438,179 A | * | 3/1984 | Solc ........................... 252/62.54 |
| 4,452,773 A | | 6/1984 | Molday ....................... 210/632 |
| 4,508,625 A | | 4/1985 | Graham ..................... 435/173.9 |
| 4,582,622 A | | 4/1986 | Ikeda et al. ................. 436/526 |
| 4,628,037 A | | 12/1986 | Chagnon et al. ............ 436/526 |
| 4,672,040 A | | 6/1987 | Josephson ................... 424/408 |
| 4,695,392 A | | 9/1987 | Whitehead et al. ......... 436/526 |
| 4,701,326 A | | 10/1987 | Nelsen et al. ............... 436/526 |
| 4,707,523 A | * | 11/1987 | Chang et al. ................ 525/372 |
| 4,735,904 A | * | 4/1988 | Starr ........................... 436/74 |
| 4,752,458 A | | 6/1988 | Robinson .................... 423/338 |
| 4,795,698 A | | 1/1989 | Owen et al. ................. 435/4 |
| 4,886,642 A | | 12/1989 | Starr ........................... 422/58 |
| 4,992,377 A | | 2/1991 | Saxholm ..................... 435/299 |
| 5,091,206 A | | 2/1992 | Wang et al. ................. 427/128 |
| 5,234,991 A | | 8/1993 | Tayot et al. ................ 525/54.1 |
| 5,262,176 A | | 11/1993 | Palmacci et al. ............ 424/9 |
| 5,358,702 A | | 10/1994 | Unger ......................... 424/9 |
| 5,420,008 A | | 5/1995 | Nishida et al. .............. 435/4 |
| 5,445,970 A | | 8/1995 | Rohr ........................... 436/526 |
| 5,472,648 A | | 12/1995 | Alisch et al. ................ 264/9 |
| 5,487,888 A | | 1/1996 | Mandeville, III et al. ... 424/78.1 |
| 5,512,332 A | | 4/1996 | Liberti et al. ............... 427/550 |
| 5,557,401 A | | 9/1996 | Maeda et al. ............... 356/73.1 |
| 5,564,104 A | | 10/1996 | Pourfarzaneh ............... 588/20 |
| 5,567,451 A | | 10/1996 | Rinn et al. .................. 426/13 |
| 5,594,136 A | | 1/1997 | Sessler et al. ............... 540/472 |
| 5,595,913 A | | 1/1997 | Lawlor et al. ............... 436/17 |
| 5,646,263 A | * | 7/1997 | Ekenberg et al. .......... 536/25.4 |
| 5,746,999 A | * | 5/1998 | Gries et al. ................. 424/322 |
| 5,834,121 A | | 11/1998 | Sucholeiki et al. ......... 428/407 |
| 5,846,530 A | | 12/1998 | Soon-Shiong et al. ..... 424/93.7 |
| 5,855,790 A | | 1/1999 | Bradbury et al. ........... 210/676 |
| 6,020,210 A | * | 2/2000 | Miltenyi ..................... 436/526 |
| 6,027,945 A | | 2/2000 | Smith et al. ................ 436/526 |

OTHER PUBLICATIONS

Solmetex, Inc., Metall: X Capabilities and Technical Specifications (1998).
Yamanishi, H., et al., Clinical Chemistry, vol. 43:12, (1997), pp. 2413–2417.
Davies, J.J., et al., Applied Biochemistry and Biotechnology, vol. 68(1–2), 1997, pp. 95–112.
Jacobs, J.C., et al., Clinical Chemistry, vol. 36, (1990), pp. 1803–1807.
J&S Medical Associates, Iron Saturating Reagents Package Insert 1988.
Huebers, H.A., et al., Clinical Chemistry, vol. 33, (1987), pp. 391–395.
Williams, H.L. et al., Clinica Chimica Acta, vol. 37, (1972), pp. 131–140.
O'Malley, J.A. et al., Clinica Chemistry, vol. 16, (1970), pp. 92–96.
Henry, R.J., Clinical Chemistry, (1964), pp. 391–395.
Ramsay, W.M.M., Clinica Chemica Acta, vol. 2, (1957), pp. 221–226.
Magaphase Advertising Material (date unknown).

* cited by examiner

*Primary Examiner*—Jill Warden
*Assistant Examiner*—Yelena Gakh
(74) *Attorney, Agent, or Firm*—Fish & Richardson P.C.

(57) ABSTRACT

Methods, reagents and reaction mixtures for determining total iron binding capability is disclosed.

15 Claims, No Drawings

RAPID SEPARATION ASSAY FOR TOTAL IRON BINDING CAPACITY

This application claims benefit to U.S. application Ser. No. 60/095,107 filed Aug. 3, 1998.

BACKGROUND OF THE INVENTION

The invention relates to methods and reagents for determining iron binding capacity in a sample, e.g., total iron binding capacity (TIBC) in a sample.

In order to assess a patient's status in terms of iron-deficiency anemia, it is common practice to measure two blood parameters: (1) serum Fe concentration and (2) serum TIBC.

Since iron exists in the blood only bound to proteins (primarily transferrin and ferritin), it is useful to know the total amount of (bound) iron plus the maximum potential for a patient to bind additional iron which may be given as a supplement to people who have iron deficiency.

Total iron (Fe) is commonly measured simply by lowering the pH to release all the iron from the binding proteins and then allowing the ionized iron, the Fe++ and Fe+++ forms, to react with a dye, e.g. ferene or ferrozine, which forms a colored complex that is directly related to the serum iron concentration.

TIBC is an additional measurement which measures the total capacity of the sample to bind iron—this number includes any sites which are bound to iron as well as to sites which are not occupied by iron but which could be so occupied. Typically only about one third of the possible iron binding sites in serum are saturated under normal conditions.

SUMMARY OF THE INVENTION

Accordingly, in one aspect, the invention features, a method of evaluating a sample, e.g., to determine TIBC. The method includes:

providing a sample;

contacting the sample (under conditions wherein iron binds to the iron binding sites in the sample) with a sufficient amount of iron such that the iron binding sites (e.g., iron binding sites on serum proteins) in the sample are saturated with iron;

sequestering the free iron in the sample to form a TIBC sample phase (e.g., a supernatant) which does not include the sequestered free iron;

evaluating the amount of concentration of iron in the TIBC sample phase, thereby of evaluating a sample, e.g., to determine TIBC In another aspect, the invention features, a method of evaluating a sample, e.g., to determine TIBC. The method includes:

providing a sample, e.g., a serum sample;

contacting the sample (under conditions wherein iron binds to the iron binding sites in the sample) with a sufficient amount of iron such that the iron binding sites (e.g., iron binding sites on serum proteins) in the sample are saturated with iron;

contacting the sample with a magnetically responsive particle (MRP) which includes an iron binding ligand;

applying a magnetic field to the sample, thereby forming a TIBC sample phase, e.g., a supernatant, which does not include the MRP;

evaluating the amount of concentration of iron in the TIBC sample phase, thereby of evaluating a sample to determine TIBC In another embodiment the high iron concentration solution is added to the sample, allowed time to saturate all the available sites. After this step the MRP's are added.

In a preferred embodiment the MRP's and high iron concentration solution are mixed, and used as a single reagent. In this embodiment the affinity of iron for the sites in the sample, e.g., serum protein sites, is much greater than the affinity of iron for the solid-phase ligand.

In another embodiment the MRP's and the sample are first combined, then the high Fe concentration solution is added.

In another aspect, the invention includes, a preparation of a reagent disclosed herein.

In another aspect, the invention includes, a reaction mixture disclosed herein, e.g., a reaction mixture which includes a sample and one or more reagents disclosed herein.

Methods, reagents, and reaction mixtures of the invention provide advantageous methods of determining TIBC. TIBC methods of the invention can (a) eliminate centrifugation, (b) be rapid, (c) use small amounts of serum (e.g., less than 500 uL), and (d) can be adapted to on-line automation or semi-automation.

All publications, patent applications, and patents cited herein are incorporated by reference. Other features and advantages of the invention will be apparent from the following description and from the claims.

DETAILED DESCRIPTION

Sample

The preferred sample is serum, but plasma can be used as well. Suitable sample sizes are less than 1,000, more preferably less than 100 microliters. They can be 10–500, more preferably 5–10, or 50–75 microliters in volume.

Sequestration

Embodiments or the invention allow the determination TIBC in a sample, without a centrifugation step.

The free iron in a sample can be sequestered by contacting the sample with an iron binding ligand which is coupled to an insoluble substrate. The insoluble substrate can serve to separate the sample into a TIBC phase and a phase which includes sequestered Fe. In embodiments of the invention the partition into phases is effected without centrifugation and/or with out removing either phase from the container which holds the sample. By way of example, the particle can be a relatively dense particle which, by virtue of its density, settles to the bottom of the vessel which contains the sample. In a particularly preferred embodiment the insoluble substrate is a manipulable substrate, e.g., a substrate which can be manipulated by a magnetic field. It is particularly preferred to use magnetically responsive particles (MRP's) which includes an iron binding ligand.

A wall or other surface of a vessel which contains the sample can also serve as the insoluble substrate. An iron binding ligand can be located on such surface or on a substrate bound to such a surface. Thus, the wall of a test tube, cuvette, sample well. e.g., the well of a micro titre plate, a capillary tube or pipette tip, can serve as an insoluble substrate to which an iron binding ligand is affixed. A substrate which is insoluble in the sample and which can allow the partition of the sample into a TIBC phase and a phase which includes sequestered Fe can be used.

Iron Binding Ligands

Chelating agents are a preferred iron binding ligand. Other suitable iron binding ligands include porous one way membranes, ion absorbers (e.g., alumina, crown ether, and dendrimers) and ion exchange resins. Preferred iron binding ligands include polyacrylic acid, deferoxamine, EDTA, EGTA, NTA, HEDTA, and other iron-binding iminocarboxylic acids, citric acid and other iron-binding carboxylic acids, tartaric acid, malonic acid, succinic acid, and tricarballylic acid. The ligand does not need to be specific for iron as long as it absorbs $Fe^{++}$ or $Fe^{+++}$ or both. The ligand bound to the insoluble substrate should be capable of sequestering all of the $Fe^{++}$ and $Fe^{+++}$ in the sample. Ligands which have an affinity for iron which is sufficiently high to strip iron from the sites in the sample, e.g., sites on serum proteins, should be avoided.

Magnetically Responsive Particles (MRP's)

MRP's are particles which respond to a magnetic field. In preferred embodiments of the invention the insoluble substrate to which an iron binding ligand is attached is am MRP. MRP's which include an iron binding ligand are added to the sample. The free iron is bound to the MRP's and a magnetic field is applied to the sample to partition the MRP's, e.g., by bringing them to the bottom of the sample container, and to form a phase which is free of MRP's, the TIBC phase. The iron in the TIBC phase is then measured.

An MRP can be made by the entrapment or precipitation of iron, nickle or cobalt salts in the particle rendering the particle paramagnetic. The particles should not release or leach free iron. A suitable example is a particle made from styrene co-polymerized with acrylic acid in the presence of an iron, nickle or cobalt salt which are encapsulated with an additional co-polymerized surface layer. Similar particles are available commercially as ESTRAPOR® superpramgnetic particles.

Other suitable particles are those which are the product of the polymerization of monomers such as methacylate, divinylbenzene, acrylamide, acrylic acid, or polyethylene in various combinations and proportions. Polymerization should be performed in the presence of iron, nickle or cobalt salts and an additional polymerization step should be used to encapsulate the particles.

Other MRP's include particles of cellulose, agarose, or other polysaccharides with an iron, nickle or cobalt salt precipitated within the particle. These particles can be washed in strong acid to remove surface iron, nickle or cobalt which could leach form the particle. An example of such a particle is sold by Cortex under the name MAG-CELL®.

Iron, nickle or cobalt can also be covalently attached to a particle.

Iron chelating polymers can be used as iron binding ligands in methods of the invention. U.S. Pat. No. 5,487,888 and U.S. Pat. No. 3,899,472 describe a variety of chelating polymers. These polymers can be used to encapsulate magnetic particles for use in methods described herein.

The particle is preferably less than 1,000, and more preferrably lsess than 10 or 1 micorn in diameter.

Generally, magnetic particles described in U.S. Pat. No. 5,595,913 can be used in the methods describe herein.

Measurement of Iron

Iron in a sample can be measured, e.g., with a colorometric method. For example, the sample can be reacted with a dye, e.g., ferene or ferrozine, or other pyridyl or phenanthroline dyes which form colored complexes with iron.

Determination of TIBC

The following method can be used to measure TIBC.

(1) a high Fe concentration solution (e.g., a saturated solution), at>pH 7.0, is mixed with the serum. The solution is added to the serum at a pH which is high, e.g.>7.0; usually approx. 8.0 and contains a high concentration of iron in the $Fe^{++}$ and $Fe^{+++}$ form. Under these conditions the added iron binds to the serum iron binding proteins to "saturate" any available binding sites;

(2) incubate for 5 minutes;

(3) a slurry of MRP's which are coated with ligands that bind iron is added;

(4) incubate for 5 minutes;

(5) a magnet is put into contact with the sample tube, and the iron which did not attach to the serum proteins (which is sequestered on the MRP's) is pulled from suspension/solution;

(6) measure the supernatant Fe to determine the TIBC of the sample.

The method need not be performed in any particular sequence of steps.

For example, the high Fe concentration solution can be added to the sample, e.g., serum, first, allowed time to saturate all the available sites. After this step the MRP's are added to remove the excess iron, the sample incubated, a magnetic field applied, and a measurement of supernatant iron made.

In a preferred embodiment the MRP's and high Fe concentration solution are mixed, and used as a single reagent. The sample, e.g., serum, is added to this reagent and allowed time for the iron to transfer to the available sites on the serum proteins, a magnetic field applied, and a measurement of supernatant iron made. In this embodiment the affinity of iron for the sites in the sample, e.g., serum protein sites, is much greater than the affinity of iron for the solid-phase ligand.

In another embodiment the MRP's and the sample, e.g., serum, are first combined, then the high Fe concentration solution is added (wherein the serum proteins and the magnetically bound ligands compete for the excess iron the sample allowed to incubate, a magnetic field applied, and a measurement of supernatant iron made.

Other embodiments are within the following claims.

What is claimed is:

1. A method of determining the TIBC of a sample, comprising:

providing a sample containing a plurality of molecules of a serum protein having at least one iron binding site;

contacting the sample with a sufficient amount of iron such that the at least one iron binding site of each of the plurality of molecules of the serum protein in the sample is saturated with iron, thereby forming a first complex comprising iron bound to the serum protein, with excess iron present in the sample remaining unbound;

contacting the sample with a MRP which includes an iron binding ligand to bind excess unbound iron in the sample with the MRP, thereby forming a second complex comprising iron and the MRP;

applying a magnetic field to the sample, thereby forming a TIBC sample phase, which includes the first complex and does not include the second complex; and evaluating the amount of iron in the TIBC sample phase, thereby determining TIBC.

2. The method of claim 1, wherein the sample is about 10 µl to about 1,000 µl.

3. The method of claim 1, wherein the sample is contacted with a high iron concentration solution.

4. The method of claim 3, wherein the sample is contacted with the high iron concentration solution and the MRP simultaneously.

5. The method of claim 4, wherein the high iron concentration solution and the MRP are mixed and used as a single reagent.

6. The method of claim 1, wherein the sample is contacted with the high iron concentration solution prior to contacting the sample with the MRP.

7. The method of claim 1, wherein the sample is contacted with the MRP prior to contacting the sample with the high iron concentration solution.

8. The method of claim 1, wherein the iron-binding ligand is selected from the group consisting of polyacrylic acid, deferoxamine, EDTA, EGTA, NTA, HEDTA, iminocarboxylic acid, citric acid, carboxylic acid, tartaric acid, malonic acid, succinic acid and tricarballyic acid.

9. The method of claim 1, wherein the iron-binding ligand comprises a porous one way membrane.

10. The method of claim 1, wherein MRP is selected from the group consisting of iron, nickel, cobalt and combinations thereof.

11. A method of determining the TIBC of a sample, comprising:

providing a sample containing a plurality of molecules of a serum protein having at least one iron binding site;

contacting the sample with a sufficient amount of iron such that the at least one iron binding site of each of the plurality of molecules of the serum protein in the sample is saturated with iron, thereby forming a first complex comprising iron bound to the serum protein, with excess iron present in the sample remaining unbound;

providing a sample containing a plurality of an iron-binding species having at least one iron binding site;

contacting the sample with a sufficient amount of iron such that the at least one iron binding site of each of the plurality of the iron-binding species in the sample is saturated with iron, thereby forming a first complex comprising iron bound to the iron-binding species, with excess iron present in the sample remaining unbound;

contacting the sample with a MRP which includes an iron binding ligand to bind excess unbound iron in the sample with the MRP, thereby forming a second complex comprising iron and the MRP;

applying a magnetic field to the sample, thereby forming a TIBC sample phase, which includes the first complex and does not include the second complex; and evaluating the amount of iron in the TIBC sample phase, thereby determining TIBC, wherein the MRP is selected from the group consisting of iron, nickel and cobalt, and the iron binding ligand is selected from the group consisting of chelating agents, porous one way membranes, ion absorbers and ion exchange resins.

12. The method of claim 11, wherein the iron binding ligand comprises a porous one way membranes.

13. The method of claim 11, wherein the iron binding ligand comprises an ion absorber.

14. The method of claim 11, wherein the iron binding ligand comprises a chelating agent.

15. The method of claim 11, wherein the iron binding ligand comprises an ion exchange resin.

* * * * *

UNITED STATES PATENT AND TRADEMARK OFFICE
CERTIFICATE OF CORRECTION

PATENT NO.    : 6,368,866 B1
DATED         : April 9, 2002
INVENTOR(S)   : Joseph F. Lawlor, Joseph D. Musto and Gordon Seik It is certified that error appears in the above-identified patent and that said Letters Patent is hereby corrected as shown below:

<u>Column 2,</u>
Line 37, "or" should be -- of --.
Line 45, "with out" should be -- without --.

<u>Column 3,</u>
Line 18, "am" should be -- an --.
Line 58, "lsess" should be -- less --; "micorn" should be -- micron --.

Signed and Sealed this

First Day of October, 2002

Attest:

JAMES E. ROGAN
Attesting Officer    Director of the United States Patent and Trademark Office